US012576036B1

(12) United States Patent
Alsayegh et al.

(10) Patent No.: US 12,576,036 B1
(45) Date of Patent: Mar. 17, 2026

(54) MARINE ORGANISM INFUSED EFFERVESCENT TABLET FOR PRODUCING ENHANCED SUSPENSIONS

(71) Applicant: KUWAIT UNIVERSITY, Safat (KW)

(72) Inventors: Naser Alsayegh, Safat (KW); Fatemah M. Safar, Safat (KW); Manal A. Alkandari, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 19/324,663

(22) Filed: Sep. 10, 2025

(51) Int. Cl.
*A61K 9/20* (2006.01)
*A61K 9/46* (2006.01)

(52) U.S. Cl.
CPC .......... *A61K 9/2095* (2013.01); *A61K 9/0007* (2013.01); *A61K 9/2009* (2013.01); *A61K 9/2013* (2013.01); *A61K 9/2068* (2013.01)

(58) Field of Classification Search
CPC ............................ A61K 9/2068; A61K 9/0007
See application file for complete search history.

(56) References Cited

U.S. PATENT DOCUMENTS

| | | | |
|---|---|---|---|
| 11,866,610 | B2 | 1/2024 | Alsayegh et al. |
| 12,012,332 | B1 | 6/2024 | Alsayegh et al. |
| 12,129,173 | B2 | 10/2024 | Alsayegh et al. |
| 12,139,666 | B1 | 11/2024 | Alsayegh et al. |
| 12,139,795 | B1 | 11/2024 | Alsayegh et al. |
| 2010/0233111 | A1 | 9/2010 | Wang et al. |

FOREIGN PATENT DOCUMENTS

| | | |
|---|---|---|
| CN | 103976933 B | 6/2016 |
| CN | 107373273 A | 11/2017 |
| JP | 07275687 A | 10/1995 |
| WO | 20200201439 A1 | 10/2020 |

OTHER PUBLICATIONS

Liegertova, M. and Maly, J., "Gastropod mucus: Interdisciplinary perspectives on biological activities, applications, and strategic priorities." ACS Biomaterials Science & Engineering 9.10 (2023): 5567-5579.
McDermottt, Maxwell et al. "Advancing discovery of snail mucins function and application." Frontiers in bioengineering and biotechnology 9 (2021): 734023.
Ali, N. et al., "Effervescent tablets for carbon-based nanofluids production," Journal of Molecular Liquids 390(B): 123083 (2023).
Ali, N. et al., "Carbon-based Nanofluids and Their Advances towards Heat Transfer Applications—A Review," Nanomaterials 11(6): 1628 (2021).
Ali, N. et al., "A Review on Nanofluids: Fabrication, Stability, and Thermophysical Properties," J. Nanomaterials 6978130 (2018).

*Primary Examiner* — James W Rogers
(74) *Attorney, Agent, or Firm* — Nath, Goldberg & Meyer; Joshua B. Goldberg

(57) ABSTRACT

An effervescent tablet including a marine-derived biosurfactant and zinc oxide particles and a method of manufacturing the effervescent tablet are provided. The method includes providing a biosurfactant derived from nudibranch mucus, providing a ZnO powder, mixing the biosurfactant and the ZnO powder under a first set of controlled conditions to form a first mixture, adding malic acid and potassium carbonate to the first mixture to obtain a second mixture, mixing the second mixture under a second set of controlled conditions, and then consolidating the second mixture into a tablet form using a hydraulic tablet press. The effervescent tablets may be added to deionized water to start a chemical reaction resulting in the formation of improved suspensions.

19 Claims, 3 Drawing Sheets

MARINE ORGANISM INFUSED EFFERVESCENT TABLET FOR PRODUCING ENHANCED SUSPENSIONS

BACKGROUND OF THE INVENTION

Field of the Invention

The disclosure of the present patent application relates to suspensions and, particularly, to a marine organism infused effervescent tablet for producing enhanced suspensions.

Description of Related Art

Suspensions are advanced fluids engineered by dispersing particles of millimeter or nanometer size within a conventional base fluid, e.g., water, ethylene glycol, or an oil. When a suspension is fabricated using micrometer-sized particles, it is referred to as a 'Microfluid'. Suspensions produced using nanometer-sized particles are commonly referred to as 'Nanofluids'. These innovative liquids have significantly enhanced properties as compared to their conventional counterparts, making them highly effective in various applications, such as soil treatment, medical diagnostics, solar collectors, liquid cooled computers, air conditioning (AC) systems, and the like.

Regarding heat transfer suspension, there are two main approaches for producing heat transfer suspensions. The first route is known as the one-step (or single-step) method, while the second technique is called the two-step method.

In the single-step approach, the particles are formed and dispersed within the hosting fluid in a single stage. The advantages of this approach generally include: (1) the suspension has higher dispersion physical stability; and (2) this approach avoids the need to transport and store dry powders. A downside of the one-step method of production is that this approach is always associated with residuals that are hard to remove, due to incomplete reactions. Further, the one-step method can only be used to fabricate specific combinations of particles and base fluids.

On the other hand, the two-step method uses pre-prepared powders, which are added and dispersed in any non-dissolving base fluid through a mixing device, such as an ultrasonicator, homogenizer, and/or magnetic stirring. The advantages of this approach include: (1) any type of suspension can be manufactured; (2) the method may be performed easily by users with a minimum level of experience; (3) the powders used are commercially available on a wide scale; and (4) these methods can be used for both small-scale and large-scale production. Due to these advantages, the two-step method of production has generally been favored by researchers working in the field of heat transfer suspensions. However, suspensions made using the two-step method generally have a lower level of physical stability compared to those fabricated through the one-step method.

The key factors impacting the successful formation of any specific suspension for a specific purpose include selecting particles with particular desired properties and a particular desired dispersion stability within the base liquid to be used. For heat transfer applications, the selection of the particles is primarily based on their thermal conductivity. As such, researchers usually focus on carbon-based materials, such as carbon nanotubes and graphene, for preparing heat transfer suspensions. For agriculture and soil treatment applications, scientists prefer the use of silicon dioxide for improving water retention and plant stress resistance, nano-clay for enhancing the cationic exchange capacity and water retention, zinc oxide for activating plant enzyme, iron oxide for enhancing the iron availability for plants, calcium carbonate for buffering the soil pH and calcium supply, biochar for increasing the organic matter and improving the microbial activity in soil, and chitosan for boosting soil microbial growth and plant immunity. Additionally, the unique photothermal properties of carbon-based suspensions make them an excellent choice for solar-thermal applications.

In terms of dispersion stability, many suspensions lack sufficient physical stability, either in their short-term or long-term shelving lifespan. This is because the dispersed particles have high surface energy, which causes them to agglomerate and cluster with each other. As a result, they tend to separate from the hosting liquid. The dispersed particles separation mechanism can demonstrate a floating or settling (sedimentation) behavior. To overcome this, scientists have used different methods to stabilize the suspensions. Examples of these enhancement methods include increasing the mixing duration and intensity, introducing surfactant to the base fluid to change its ionic charge, and/or functionalizing (or oxidizing) the dry powder before dispersing it within the base fluid.

When considering surfactants as a dispersion improvement option, they must be selected based on several important factors, such as their compatibility with the particles, their compatibility with the base fluid, and the targeted application. Compatibility with the particle surface chemistry is crucial, as different materials such as metal oxides, carbon-based particles, or metallic particles may require specific surfactant types. The polarity of the base fluid, whether it is water, oil, or ethylene glycol, also plays a significant role in determining the appropriate surfactant. The target application, whether biomedical or industrial, will influence the choice, as requirements for biocompatibility, toxicity, and performance can vary widely. The surfactant must also provide the necessary thermal and chemical stability for the intended operating conditions. Environmental and toxicity concerns, particularly for applications involving biological systems, must be carefully evaluated. In addition, cost constraints are often a practical consideration, especially for large-scale or commercial applications.

In general, a surfactant is classified both by charge (i.e., as (a)"anionic", or negatively charged; (b) "cationic", or positively charged; (c) "non-ionic", or no net charge; or (d) "Zwitterionic" (amphoteric), a single molecule have both positive and negative charges) and by origin (i.e., as (a) "biological", used to refer to biosurfactants; or (b) "synthetic", used to refer to non-biological or chemical surfactants).

Anionic surfactants carry a negative charge on their hydrophilic head and are particularly effective with positively charged or neutral nanoparticles. Common examples include sodium dodecyl sulfate (SDS), sodium lauryl sulfate (SLS), and sodium stearate. They are widely applied in stabilizing metal oxide nanoparticles, such as aluminum oxide and titanium dioxide, in water. Their advantages include strong electrostatic repulsion and cost-effectiveness; however, they are sensitive to the pH and ionic strength of the solution.

Cationic surfactants, in contrast, carry a positive charge and are effective with negatively charged nanoparticles. Examples include cetyltrimethylammonium bromide (CTAB), cetylpyridinium chloride (CPC), and dodecyltrimethylammonium bromide (DTAB). These surfactants offer strong binding to negatively charged surfaces but may pose toxicity concerns in biological applications and their stability can be compromised by competing ions.

Non-ionic surfactants have no net charge, relying primarily on steric hindrance for stabilization, making them suitable for systems sensitive to pH changes or high ionic strength. Common non-ionic surfactants include the Tween series (20, 40, 60, and 80), Triton X-100, Span series (20 and 80), and Pluronic F127. Their advantages include good thermal and ionic stability and low toxicity, which makes them ideal for biomedical suspensions, although they can be less effective for very high surface-energy nanoparticles.

Lastly, zwitterionic surfactants possess both positive and negative charges on different parts of the molecule and can behave as anionic or cationic depending on the pH level of the solution. Examples include lecithin (a phospholipid) and betaine derivatives like cocamidopropyl betaine. These surfactants offer excellent stability over a wide pH range and are generally mild and biocompatible, but they are typically more expensive compared to other types.

On the other hand, biological surfactants (biosurfactants) are naturally produced by microorganisms such as bacteria and yeast, with common examples including rhamnolipids, sophorolipids, and surfactin. They are highly biodegradable, exhibit low toxicity, and offer good stability across a range of conditions, making them particularly suitable for medical and environmental suspension applications. However, their production costs are generally higher compared to synthetic alternatives. In this regard, non-biological surfactants (synthetic surfactants) like sodium dodecyl sulfate (SDS), cetyltrimethylammonium bromide (CTAB), and triton X-100 are chemically synthesized, often more cost-effective, and widely used in industrial, mechanical, and electronic nano-fluids. Their biodegradability and toxicity vary, with many synthetic surfactants showing higher environmental and biological risks.

In addition to the biological and synthetic types of surfactants, bioinspired surfactants have recently gained wide attention. These are designed to mimic the structure and functionality of natural surfactants, aiming to combine high stability with low toxicity, especially for use in medical and green energy applications. Examples of bioinspired surfactants include peptide-based surfactants, protein-polymer conjugates, and plant-extracted saponins.

Many marine organisms can be used as biosurfactants for enhancing the physical stability of suspensions. These hidden assets are rarely looked at although they are considered sustainable and can easily be obtained. For example, the gastropod nudibranchs (meaning naked gills) in the phylum Mollusca are a fascinating group of soft-bodied marine invertebrates belonging to the sub-class Heterobranchia and order Nudibranchia that shed their shells after their larval stage. They are also known as sea slugs and some of the ocean's most attractive colorful creatures that gain their color from the food they consume. These creatures leave a trail of slime behind them, which is a unique marker filled with chemicals used to communicate with other nudibranchs to find a potential partner to mate with or even warn others of potential danger. Nudibranchs are also known for their wide availability within the ocean and on the coast, generating mucus as part of their defense and movement mechanism as well as feeding and reproduction protocols. This mucus contains basic proteins, peptides, ammonia, sulfur, and other valuable minerals. Moreover, the generated mucus can cause either acidic or alkaline effects on the surrounding liquid environment. Each nudibranch can extract between 10 μL to 1 mL of mucus, depending on its size (i.e., 1 cm to >7 cm) and excitement condition.

For agriculture applications, micro and nano scaled particles and biosurfactants are favorable for enhancing soil health. This is due to these particles' large surface area, which enhances adhesion between soil particles and contributes to stronger soil structures, and simulation of microbial activity caused by the biological surfactant as well as its high mucopolysaccharides and glycoproteins content. Madadi et al. ("Soil improvement in Qom City under the influence of montmorillonite nanoclay", *Int. J. Geo-Engineering*, 16:11 (2025)) evaluated soil stability after adding nanoclay using direct shear tests and observed a significant improvement in cohesion—up to 12 times higher—and a 15% increase in the internal friction angle. This improvement was attributed to enhanced adhesion between soil particles, leading to agglomeration and the formation of stronger soil structures.

Moreover, Kermanipour et al. ("Mechanical and Microstructural Characterization of a Non-stabilized Sandy Soil," *Geotechnical and Geological Engineering*, 42: p. 6131-6146 (2024)) demonstrated that adding nanoparticles improved the efficiency of soil additives such as ground granulated blast furnace slag (GGBS) and recycled glass powder (RGP) in enhancing soil strength and durability. They observed up to a 2-fold increase in soil strength when 2% nano-aluminum silicate was added to GGBS-stabilized soil.

Mohammadi et al. ("Experimental and Numerical Evaluation of the Effect of nano Calcium Carbonate on Geotechnical Properties of Clayey Sand Soil", *KSCE Journal of Civil Engineering*, 26(1): pp. 35-46 (2022)) showed that soil stability can be improved from 15 kPa to 40 kPa, when adding 0.7% nano-calcium carbonate. This enhancement results from the formation of cementitious calcium-silicate-hydrate (C—S—H) crystals, which strengthen inter-particle bonding and thereby improve the material's overall structural integrity.

Cheraghalikhani et al. ("Mirco- and nano-Illite to improve strength of untreated-soil as a nano soil-improvement (NSI) technique", *Scientific Reports*, 14: 10862 (2024)) found that nanoclay particles were 3.5 times more effective than micro-clay particles in enhancing soil stabilization, as measured by the increase in unconfined compressive strength (UCS). The reason for this variation was attributed to the differences in morphology and surface area between the two sizes.

The unique properties of micro and nano scaled materials, such as their high specific surface area, high dispersion and high cation exchange capacity, render them effective in enhancing soil fertility by improving both water retention and nutrient holding capacity. According to Kale et.al., ("Effectiveness of nanoparticles in improving soil fertility and eco-friendly crop resistance: A comprehensive review," *Biocatalysis and Agricultural Biotechnology*, 56: 103066 (2024)), nano-fertilizers exhibit reduced leaching and nutrient loss due to their strong adsorption forces, a result of their high surface area. Further, Zhao et al. ("Use of Carbon Nanoparticles to Improve Soil Fertility, Crop Growth and Nutrient Uptake by Corn (*Zea mays* L.)," *Nanomaterials*, 11(10): 2717 (2021)) demonstrated that nano carbon is a significant solution for enhancing nutrient retention. They observed an approximately threefold increase in available nitrate in Spodosol soil when nano carbon was applied at 400 mg/kg. Additionally, available phosphorus increased by about 18 times at an application rate of 800 mg/kg, which was attributed to the high surface area of nano carbon. Lastly, Mahmoud et al. ("Enhancing Maize Yield and Soil Health through the Residual Impact of Nanomaterials in Contaminated Soils to Sustain Food," *Nanomaterials*, 14(4): 369 (2024)) observed an improvement in cation exchange capacity, which enhanced nutrient retention ($Ca^{2+}$, $Mg^{2+}$, $K^+$) and reduced soil salinity because of the replacement of sodium ions by $Ca^{2+}$ and $Mg^{2+}$.

Researchers can currently use a variety of different methods to characterize the physical stability of their fabricated suspensions, including: (1) the sedimentation photographical capturing method; (2) Dynamic Light Scattering (DLS); (3) Zeta potential analysis; (4) the 3-ω approach; (5) Scanning Electron Microscopy (SEM) analysis; (6) Transmission Electron Microscopy (TEM); (7) spectral analysis; (8) centrifugation; and (9) article size analysis.

One of the main challenges in the production of suspensions is their complicated fabrication process. The methods of making suspensions can require sophisticated equipment, high handling experience, and are often time consuming. As such, Ali et al. (Ali, N. et al., "Effervescent tablets for carbon-based nanofluids production," *Journal of Molecular Liquids,* 390(B): 123083 (2023)) and Alsayegh et al. (U.S. Pat. No. 11,866,610 B2) developed a new method to overcome the obstacles that were associated with the conventional suspension preparation method. Their method relied on the use of effervescent tablet technology, where the released gas from the effervescent agent's reaction acts as a driving force towards dispersing the accompanied particles within the base fluid, and thus forming the suspension. In comparison with the traditional suspension fabrication approach, the effervescent tablet-based method provides numerous advantages, including: (1) eliminating the need for bulky equipment-users simply dissolve the tablet in the fluid, making it portable and user-friendly; (2) accelerating nanoparticle dispersion through gas bubble agitation, ensuring uniform mixing; (3) reducing preparation time compared to sonication or high-shear mixing; (4) pre-measuring, ensuring consistent nanoparticle concentration in each batch, whereas conventional methods often suffer from batch-to-batch variability due to manual measurement errors; (5) eliminating the need for external energy input, reducing costs and environmental impact; (6) reducing the exposure risks associated with handling raw powders when compared to conventional methods involving direct handling of particles, which can lead to health hazards from inhalation; (7) ease of scaling up for industrial applications due to pre-packaged and easy-to-use format; (8) ideally suited for on-site preparation without specialized laboratory equipment; (9) allowing for custom formulations by incorporating multiple particle types, surfactants, and additives in a single tablet; and (10) reducing the need for separate chemical processing for multi-particle suspensions. However, further materials and/or processes remain necessary to aid in the creation of certain types of suspensions.

Thus, new methods of making improved effervescent tablets, as well as the improved effervescent tablets themselves, are desired.

SUMMARY OF THE INVENTION

The present disclosure relates to an effervescent tablet including a marine-derived biosurfactant and zinc oxide (ZnO) particles and a method of manufacturing the effervescent tablet. The method includes providing a biosurfactant derived from nudibranch mucus, providing a ZnO powder, mixing the biosurfactant and the ZnO powder under a first set of controlled conditions to form a first mixture, adding malic acid and potassium carbonate to the first mixture to obtain a second mixture, mixing the second mixture under a second set of controlled conditions, and then consolidating the second mixture into a tablet form using a hydraulic tablet press.

In an embodiment, the nudibranch mucus may be provided in a powdered, freeze-dried form. In an alternative embodiment, the nudibranch mucus may be provided in a concentrated form. In some embodiments, the nudibranch mucus may be derived from a plurality of nudibranchs.

In certain embodiments, the present effervescent tablets can comprise: a marine-derived biosurfactant; zinc oxide powder; malic acid; and potassium carbonate.

In some embodiments, the present effervescent tablets may be added to 1 L of deionized water (DIW) to start a chemical reaction resulting in the formation of 0.1 vol. %, 0.5 vol. %, or 1 vol. % suspensions.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Definitions

Figure 1:
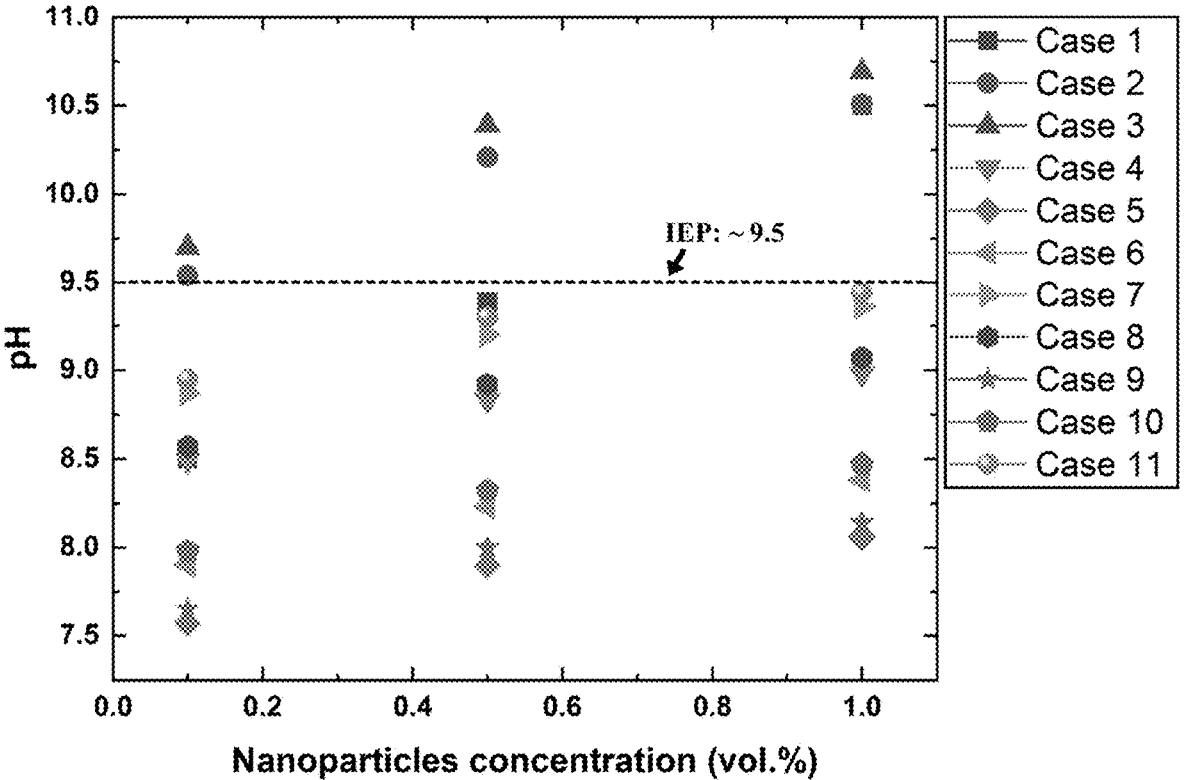
FIG. 1 depicts a graph displaying pH variation and dispersed particle concentration of various examples of the present methods.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present disclosure relates to an effervescent tablet including a marine-derived biosurfactant (i.e., nudibranch mucus) and zinc oxide (ZnO) particles and a method of manufacturing the effervescent tablet. The method includes providing a biosurfactant derived from nudibranch mucus, providing a ZnO powder, mixing the biosurfactant and the ZnO powder under a first set of controlled conditions to form a first mixture, adding malic acid and potassium carbonate to the first mixture to obtain a second mixture, mixing the second mixture under a second set of controlled conditions, and then consolidating the second mixture into a tablet form using a hydraulic tablet press.

In an embodiment, the nudibranch mucus may be provided in a powdered, freeze-dried form. In an alternative embodiment, the nudibranch mucus may be provided in a concentrated form. In some embodiments, the nudibranch mucus may be derived from a plurality of nudibranchs.

In an embodiment, the freeze-dried nudibranch derived biosurfactant may be mixed with ZnO powder sufficient to achieve about 0.1 vol % ZnO, about 0.5 vol % ZnO, or about 1.0 vol % ZnO within the base fluid. In a non-limiting example, about 0.3 g of freeze-dried nudibranch derived biosurfactant may be mixed with about 5.61 g, about 28.05 g, or about 56.1 g of ZnO powder to obtain the first mixture.

In an embodiment, mixing the biosurfactant and the ZnO powder under a first controlled environment may include mixing using a mortar and pestle for between about 10 minutes and about 20 minutes at a temperature of about 20° C. to about 27° C. and humidity of about 30% to about 50%. In some embodiments, the mixing may be for about 10 minutes, about 15 minutes, or about 20 minutes. In an embodiment, the mixing may be for about 15 minutes or 15 minutes.

In an embodiment, mixing the second mixture under a second controlled environment may include mixing the second mixture for between about 5 minutes and about 10 minutes using a mortar and pestle under an inert gas at a temperature between about 20° C. and about 27° C., and at about zero % humidity. In some embodiments, the second mixture may be mixed for about 5 minutes, about 6 minutes, about 7 minutes, about 8 minutes, about 9 minutes, or about 10 minutes.

In an embodiment, consolidating the second mixtures may include using a hydraulic tablet press under 100 kN to form about 25 mm (diameter) by about 5.7 mm (thickness) effervescent tablets.

In certain embodiments, the effervescent tablets made according to the present methods can comprise: a marine-derived biosurfactant; zinc oxide powder; malic acid; and potassium carbonate.

In some embodiments, the effervescent tablets may be added to 1 L of deionized water (DIW) to start a chemical reaction resulting in the formation of 0.1 vol. %, 0.5 vol. %, or 1 vol. % suspensions.

In some embodiments, the biosurfactant may not be added in powder form. Instead, about 1 wt. % of pure concentrated nudibranch mucus may be dissolved first in the DIW before adding the effervescent tablets to the DIW. Pure concentrated nudibranch mucus may be obtained by placing clean raw mucus in a sterile 2 ml microcentrifuge and centrifuging the mucus at a speed of between about 3,000 rpm and about 5,000 rpm for about 5 min to about 16 min to concentrate the bioactive components. The mucus may be centrifuged at about 3,000 rpm, about 3,500 rpm, about 4,000 rpm, about 4,500 rpm, or about 5,000 rpm for about 5 min, about 6 min, about 7, min, about 8 min, about 9 min, or about 10 min. To dissolve the 1 wt. % of pure concentrated mucus in the DIW, a probe sonicator may be placed in the vial containing the mucus and the DIW and run for about 1 h or more. In these embodiments, the method may include providing a ZnO powder; adding malic acid and potassium carbonate to the ZnO powder to obtain a mixture; mixing the mixture under a set of controlled conditions; consolidating the mixture into tablet form using a hydraulic tablet press to obtain the effervescent tablet; adding about 1 wt % concentrated nudibranch mucus to 1 liter of deionized water; sonicating the deionized water including the concentrated nudibranch mucus for about 1 hour to obtain a sonicated mixture; and adding the effervescent tablet to the sonicated mixture of deionized water and concentrated nudibranch mucus to obtain a suspension The nudibranch species *Dendrodoris fumata* is one of the nudibranchs that have significant global distribution in marine biodiversity. In some regions, they are referred to as Black Dorid and Hazy *Dendrodoris*. This species has been frequently documented in Kuwait and many other countries.

Nudibranch mucus can be used as a particle dispersion enhancer (i.e., as a biological surfactant). However, the surface charge of the selected particles needs to match that of the mucus. For instance, nano-biochar requires acidic mucus to be stabilized, whereas nano zinc oxide favors alkaline mucus to improve its dispersion level. For agriculture applications, this type of surfactant would aid in stabilizing the structure of the soil by creating an interconnection between the different soil particles. It would also increase its fertility due to its mineral contents and capability of simulating microbial activity.

The present methods may include a method of preparing a biosurfactant derived from a marine organism. The method includes providing a nudibranch of the species *Dendrodoris fumata*, stimulating production of mucus by the nudibranch, collecting the mucus from the nudibranch, concentrating the bioactive components in the mucus, determining the pH of the mucus, categorizing the mucus as acidic or alkaline, and freeze-drying the mucus.

In an embodiment, stimulating production of mucus by the nudibranch includes stimulating the nudibranch by at least one method selected from the group consisting of mild mechanical stress (such as touching by a soft brush), light exposure, and exposure to mild airflow via brief removal from the water. In a particular, non-limiting embodiment, stimulating production of mucus by the nudibranch includes all of stimulating the nudibranch by mild mechanical stress (such as touching by a soft brush), light exposure, and exposure to mild airflow via brief removal from the water.

The stimulation will disturb the nudibranch, causing it to secrete defensive mucus. The above stressing can be repeated for multiple nudibranchs, ensuring the production of an adequate quantity of mucus to increase sample volume while minimizing harm.

In an embodiment, concentrating the bioactive components found in the mucus comprises centrifuging the mucus at a speed of about 4,000 rpm for about 10 minutes.

The pH measurement step is crucial to accurately determine the mucus acidity or alkalinity levels as it can slightly deviate based on the geographical location where the nudibranch is living. The pH measurement step would also help in distinguishing between those mucus that are suitable for dispersing positive charged particles and those that are suitable for dispersing negatively charged particles. For example, negatively charged particles require alkaline mucus to be stabilized, whereas positively charged particles require acidic mucus to enhance their dispersion.

In an embodiment, determining the pH of the mucus can comprise adding about 1 wt. % of the concentrated mucus to deionized water and probe sonicating for about 1 hour under controlled temperature (23° C.) to form a suspension. The pH value of the suspension can then be measured using a pH meter to categorize each alkaline mucus and each acidic mucus. Mucus having a pH greater than 7 can be categorized as alkaline, while mucus having a pH less than 7 can be categorized as acidic.

In a further embodiment, determining the pH of the mucus may comprise predicting the pH of the mucus based upon previously observed results for the pH of mucus obtained from similar nudibranchs. For example, the pH of the mucus may be determined to be acidic for mucus obtained from white and red colored nudibranchs and to be alkaline for mucus obtained from orange and brown colored nudibranchs.

In an embodiment, freeze-drying the mucus can comprise pre-cooling the concentrated mucus for about 8 hours by placing the concentrated mucus in a sterile container held at a temperature $\leq-20°$ C.; transferring the container to a freezer held at a temperature $\leq-80°$ C. for about 12 hours to obtain frozen mucus; placing the frozen mucus in a dry-freeze system at a pressure <0.1 mbar for about 48 hours to obtain solidified mucus; placing the solidified mucus in a controlled environment under inert gas; hand milling the solidified mucus for about 15 minutes using a mortar and pestle to obtain a powder; and placing the powder in an airtight and lightproof container. The pre-cooling step starts the solidification process. The freezer held at a temperature $\leq-80°$ C. may be an ultra-low freezer. The freezer step may ensure uniform crystallization of the water content in the mucus. The system capable of maintaining pressure <0.1 mbar may be a high-vacuum dry-freeze system and may sublimate the crystallized water directly into vapor without undergoing a melting phase. The controlled environment under inert gas may be a glovebox, and this step may cause the solidified sample to take a powder form. Finally, the as-prepared powder may be placed in an airtight and light-proof container before removing it from the glovebox and stored under refrigerated temperature for later usage.

At this stage the marine organism-based biosurfactant is ready to be used as a dispersing agent during the synthesis of different types of suspensions. It is important to note that such a type of surfactant can be suitable for applications working under a temperature range between 5° C. to 65° C. Higher temperature applications may cause the biosurfactant to degrade significantly, thereby losing its effectiveness as a dispersant.

In an embodiment, preparing biosurfactant derived from a marine organism includes providing and categorizing a plurality of nudibranchs of the species *Dendrodoris fumata*, stimulating production of mucus by each of the plurality of nudibranchs, collecting a plurality of mucus from each of the plurality of nudibranchs, respectively, concentrating the bioactive components in each of the plurality of mucus, determining the pH of each of the plurality of mucus, categorizing each of the plurality of mucus as acidic or alkaline, grouping each acidic mucus together, grouping each alkaline mucus together, and freeze-drying the acidic mucus group and the alkaline mucus group, respectively.

In an embodiment, categorizing the plurality of nudibranchs may include grouping the nudibranchs by color. In a further embodiment, the nudibranchs may be categorized as red nudibranchs, orange nudibranchs, white nudibranchs, or brown nudibranchs.

In an embodiment, stimulating production of mucus by the plurality of nudibranchs includes stimulating each of the plurality of nudibranchs by at least one method selected from the group consisting of mild mechanical stress (such as touching by a soft brush), light exposure, and exposure to mild airflow via brief removal from the water. In a preferred embodiment, stimulating production of mucus by the plurality of nudibranchs includes stimulating each of the plurality of nudibranchs by mild mechanical stress (such as touching by a soft brush), light exposure, and exposure to mild airflow via brief removal from the water.

In certain embodiments, the stimulation may disturb the plurality of nudibranchs, causing them to secrete defensive mucus. The above stressing can be repeated for multiple nudibranchs, ensuring the production of an adequate quantity of mucus to increase sample volume while minimizing harm.

In an embodiment, concentrating the bioactive components found in the plurality of mucus can comprise placing each of the plurality of mucus in separate centrifuge vials and centrifuging each of the plurality of mucus at a speed of about 4,000 rpm for about 10 minutes, respectively.

The pH measurement step is crucial to accurately determine the mucus acidity or alkalinity levels as it can slightly deviate based on the geographical location where the nudibranch is living. It would also help in distinguishing between the mucus that is suitable for dispersing positive charged particles and those that are negatively charged. For example, negatively charged particles require alkaline mucus to be stabilized, whereas positively charged particles require acidic mucus to enhance its dispersion.

In an embodiment, determining the pH of the plurality of mucus comprises adding about 1 wt. % of each of the concentrated plurality of mucus to deionized water and probe sonicated for about 1 hour under controlled temperature (23° C.) to form a suspension. The pH value of the suspension is then measured using a pH meter to categorize the alkaline mucus and the acidic mucus. Mucus having a pH greater than 7 is categorized as alkaline, while mucus having a pH less than 7 is categorized as acidic.

In a further embodiment, determining the pH of the mucus may comprise predicting the pH of the mucus based upon previously observed results for the pH of mucus obtained from similar nudibranchs. For example, the pH of the mucus may be determined to be acidic for mucus obtained from white and red colored nudibranchs and to be alkaline for mucus obtained from orange and brown colored nudibranchs.

In an embodiment, freeze-drying the mucus comprises pre-cooling the acidic mucus and the alkaline mucus for about 8 hours by placing the acidic mucus and the alkaline mucus in sterile containers held at a temperature ≤−20° C.; transferring the containers to a freezer held at a temperature ≤−80° C. for about 12 hours to obtain frozen mucus; placing each frozen mucus in a dry-freeze system at a pressure <0.1 mbar for about 48 hours to obtain solidified mucus; placing each solidified mucus in a controlled environment under inert gas; hand milling each solidified mucus for about 15 minutes using a mortar and pestle to obtain powdered acidic mucus and powdered alkaline mucus; and placing each of powdered acidic mucus and powdered alkaline mucus in airtight and lightproof containers.

At this stage the marine organism-based biosurfactant is ready to be used as a dispersing agent during the synthesis of different types of suspensions. It is important to note that such a type of surfactant is suitable for applications working under a temperature range between 5° C. to 65° C. Higher temperature applications would cause the biosurfactant to degrade significantly, thereby losing its effectiveness as a dispersant.

The biosurfactants made according to the methods disclosed herein may be particularly helpful in addressing a number of concerns that arise when formulating suspensions. In particular, these methods can produce biosurfactants helpful in addressing the following: (1) Dispersion Stability Issue. Traditional suspensions, especially nanofluids and microfluids, often suffer from poor short-term and long-term dispersion stability due to particle agglomeration and sedimentation. The present methods address this by obtaining a novel marine biosurfactant derived from nudibranch mucus, which stabilizes particles in suspension. (2)

Environmental and Toxicity Concerns. Many conventional synthetic surfactants are toxic and environmentally harmful. The present methods are used to obtain biological surfactants (biosurfactants), offering a biodegradable, low-toxicity alternative. (3) Customization for Particle Type. Different particles (positively or negatively charged) need different stabilizing environments (acidic vs alkaline). The mucus-based surfactant disclosed herein can be tuned (acidic or alkaline) based on using mucus obtained from nudibranchs of different colors, allowing tailored dispersion solutions. (4) Complex Production Methods. Existing surfactants often involve complex chemical synthesis processes. The present methods use natural extraction and mild processing, making them simpler, greener, and less resource intensive. (5) Heat Sensitivity of Surfactants. Many surfactants degrade under certain conditions. The present methods are optimized for stabilizing suspensions between 5° C. to 65° C., making them suitable for obtaining biosurfactants, which can be used in many practical applications, without rapid degradation.

The marine organism derived surfactant prepared according to the present methods has a variety of potential useful applications, including in the manufacture of suspensions. Suspensions including the marine organism derived surfactant may be used in low and mid temperature range thermal applications, soil treatment and agricultural applications, biomedical applications, environmental remediation (e.g., stabilizing nanoparticles used for pollutant removal), the manufacture of coatings and paints (where stable dispersions of nanoparticles are critical), the manufacture of composite materials (for example, embedding nanoparticles into polymers, metals, or ceramics), for use in the laboratory to prepare stable micro- or nano-scaled particle suspensions for experimental and research purposes, formulating natural cosmetic products such as stabilizing emulsions (creams, lotions, serums), formulating natural skin care products that avoid synthetic chemicals, and in the food industry, for suspensions proven food-safe (e.g. stabilizing nano-encapsulated food additives, flavors, or nutrients).

When combining the effervescent tablet technology with a biosurfactant made of the mucus of nudibranch of type *Dendrodoris fumata* and nano or micro particles, an advanced form of suspension can be formed and used for many lab scale and industrial applications. An accurate calculation of the effect of the effervescent agents, particles materials, and biosurfactant on the pH of the suspension and zeta potential is required. The suspension pH should not reach the isoelectric point (IEP), and its zeta potential should remain above ±30 mV for the dispersed particles to remain physically stable.

Nudibranch mucus can be used as a particle's dispersion enhancer (i.e., biological surfactant). However, the surface charge of the selected particles needs to match that of the mucus. For instance, nano-biochar requires acidic mucus to be stabilized, whereas nano zinc oxide favors alkaline mucus to improve its dispersion level. For agriculture applications, this type of surfactant would aid in stabilizing the structure of the soil by creating an interconnection between the different soil particles. It would also increase its fertility due to its mineral contents and capability of simulating microbial activity.

While there are no direct field studies of nudibranch mucus in soils, its biochemical makeup—rich in mucopolysaccharides and glycoproteins—closely parallels other natural polymers (microbial extracellular polymeric substances (EPS), seaweed polysaccharides) that have well-documented benefits for soil health. For example, microbial EPS are well known to bind soil particles into stable aggregates. In soils, EPS act as a natural "glue" that holds mineral and organic particles together, markedly improving aggregate stability and resistance to erosion. This aggregation creates macropores that enhance aeration and root penetration and has been shown to benefit overall soil structure and fertility. By analogy, the sticky polymers in nudibranch mucus would fulfil the same role, promoting durable soil aggregates and healthier tilth.

Beyond structure, microbial EPS are highly hygroscopic: they form hydrophilic films around soil particles that retain water in the pore spaces and buffer against drought stress. Field studies of dryland biological soil crusts demonstrate that EPS can dramatically increase water-holding capacity, delaying desiccation and sustaining microbial and plant activity under low-moisture conditions. Nudibranch mucus, with its similar polysaccharide content, would eventually form comparable water-retentive matrices in the rhizosphere, helping to maintain moisture availability around seeds and roots.

The charged functional groups in microbial exopolysaccharides also bind and slowly release nutrient cations—such as $Ca^{2+}$, $Mg^{2+}$, and $K^+$—in the rhizosphere, improving nutrient use efficiency and reducing leaching losses. Seaweed-derived polymers (e.g., alginates) are already used in agriculture as bio-fertilizers for this very reason. Nudibranch mucus, rich in anionic sites, can serve as a natural nutrient reservoir, chelating micronutrients and providing a slower release source exactly where young roots need them.

Both microbial EPS and marine mucilages confer resistance to biological and abiotic stresses. EPS supports beneficial biofilms that protect soil microbes—and by extension plant roots—from salinity and pH extremes, while specific UV-absorbing and antimicrobial compounds in nudibranch mucus (e.g., mycosporine-like amino acids) can further shield seedlings from pathogen attack and photooxidative damage. Integrating such multifunctional coatings into seed treatments or soil amendments could reduce reliance on synthetic polymers and agrochemicals, offering a sustainable route to enhanced soil health and crop resilience.

The advantages of the present tablets and methods include: (1) Simplicity of the Suspension Production. It introduces effervescent tablets as a novel approach to disperse nanoparticles in a liquid medium, eliminating the need for external mixing devices. (2) Resolving the Dispersion Stability Issue. Traditional suspensions, especially nanofluids and microfluids, often suffer from poor short-term and long-term dispersion stability due to particle agglomeration and sedimentation. The present tablets and methods address this by using effervescent agents along with a novel marine biosurfactant derived from nudibranch mucus to stabilize the dispersed particles in the suspension. (3) Avoiding Environmental and Toxicity Concerns. Many conventional synthetic surfactants are toxic and environmentally harmful. In contrast, the presently described subject matter uses biological surfactants (biosurfactants), offering a biodegradable, low-toxicity alternative. (4) Advantages for Agricultural Applications. Since the mucus is rich in mucopolysaccharides and glycoproteins, it will be beneficial for soil fertilization and stabilization. On the other hand, micro and nano scaled particles are well known to improve soil health, as explained in the literature. Therefore, combining both in the form of a suspension would further enhance the soil condition for agriculture applications. (5) Scalability and Cost. The present methods allow for scalable and cost-effective production of suspensions.

The present tablets and methods may be better understood by referring to the following examples.

Example 1

Preparing ZnO Suspensions

About 0.3 g of various nudibranch derived biosurfactants prepared according to one of the methods disclosed herein were provided. The biosurfactants were mixed individually with about 5.61 g, about 28.05 g, and about 56.1 g of ZnO powder for 15 min under a first controlled environment of about 20° C. to about 27° C. and humidity of about 30% to about 50% to obtain first mixtures. These mixing conditions caused a monolayer to form on the outer particle surface. Afterwards, malic acid ($C_4H_6O_5$) and potassium carbonate ($K_2CO_3$) were added to the first mixtures to obtain second mixtures, and the second mixtures were mixed under a second controlled environment for about 5 minutes. The weight ratios of the ZnO, $C_4H_6O_5$, and $K_2CO_3$, respectively, were 1:1.94:2 and 1:2.91:3. The second controlled environment included mixing under an inert gas at a temperature between about 20° C. and about 27° C., and at about zero % humidity. Both mixing steps were conducted using a mortar and pestle.

The weight ratios used in the present methods were calculated as follows. The chemical reaction of $C_4H_6O_5$ (malic acid) and $K_2CO_3$ (potassium carbonate) produces $K_2C_4H_4O_5$ (dipotassium malate), $H_2O$ (water), and $CO_2$ (carbon dioxide). To achieve a total conversion of $C_4H_6O_5$ and $K_2CO_3$, a stoichiometric ratio of 1:1 is required. One mole of $C_4H_6O_5$ should be reacted with one mole of $K_2CO_3$ to fully convert the reactants and produce 1 mole of $CO_2$. One mole of $C_4H_6O_5$ is 134.09 g. One mole of $K_2CO_3$ is 138.21 g. One mole of $CO_2$ is 44.01 g. Therefore, 1 mole of malic acid (134.09 g) reacts with 1 mole of potassium carbonate (138.21 g) to produce 1 mole of carbon dioxide (44.01 g).

The mass ratio of malic acid to potassium carbonate is 134.09 g:138.21 g, which simplifies to about 0.97:1. This means that for a complete reaction, 0.97 grams of malic acid are required per gram of potassium carbonate. Considering the generated amount of $CO_2$ needed to physically disperse the particles, a minimum weight ratio of 1 ZnO:1.94 $C_4H_6O_5$: 2 $C_4H_6O_5$ is required. Lower mass ratios would not provide sufficient buoyant force to fully disperse the particles within the base fluid. Increasing the weight ratio would further enhance the dispersion mechanism, and therefore a weight ratio of 1:2.91:3 was also tested.

Once the second mixtures were obtained, the second mixtures were consolidated using a hydraulic tablet press under 100 kN to form about 25 mm (diameter)×about 5.7 mm (thickness) tablets. The tablets were then added to 1 L of deionized water (DIW) to start a chemical reaction resulting in the formation of 0.1 vol. %, 0.5 vol. %, and 1 vol. % suspensions. The pH level and zeta potential of the suspensions were then tested. The pH of DIW is about 7. For a suspension to be stable, its pH should be either above or lower than the dispersed particle IEP (ZnO IEP is at a pH of ~9.5), and the zeta potential value should be between 30 mV to 40 mV (or –30 mV to –40 mV). A suspension with a pH value that is equal to the dispersed particles IEP or has a zeta potential that is equal to zero cannot maintain its stability.

A first experimental set of ZnO suspensions at 0.1 vol. %, 0.5 vol. %, and 1 vol. % were prepared using 60 min bath sonication under a controlled temperature of about 25° C. in about 1 L of DIW (Case 1). A second experimental set of ZnO suspensions were prepared at similar vol. percentages using effervescent agents alone at a ratio of 1:1.94:2 (Case 2). A third experimental set of ZnO suspensions were prepared at similar vol. percentages using effervescent agents alone of ratio of 1:2.91:3 (Case 3). A fourth set of ZnO suspensions were prepared at similar vol. percentages using effervescent agents at a ratio of 1:1.94:2 and using mucus from orange nudibranchs (Case 4). A fifth set of ZnO suspensions were prepared at similar vol. percentages using effervescent agents at a ratio of 1:1.94:2 and using mucus from white nudibranchs (Case 5). A sixth set of ZnO suspensions were prepared at similar vol. percentages using effervescent agents at a ratio of 1:1.94:2 and using mucus from red nudibranchs (Case 6). A seventh set of ZnO suspensions were prepared at similar vol. percentages using effervescent agents at a ratio of 1:1.94:2 and mucus from brown nudibranchs (Case 7). An eighth set of ZnO suspensions were prepared using effervescent agents at a ratio of 1:2.91:3 and mucus from orange nudibranchs (Case 8). A ninth set of ZnO suspensions were prepared using effervescent agents at a ratio of 1:2.91:3 and mucus from white nudibranchs (Case 9). A tenth set of ZnO suspensions were prepared using effervescent agents at a ratio of 1:2.91:3 and mucus from red nudibranchs (Case 10). An eleventh set of ZnO suspensions were prepared using effervescent agents at a ratio of 1:2.91:3 and mucus from brown nudibranchs (Case 11). A summary of the tested scenarios is shown in Table 1.

TABLE 1

Summary of Test Cases

| Case no. | Effervescent agent's ratio used | Mucus from nudibranch of color |
|---|---|---|
| 1 | — | — |
| 2 | 1:1.94:2 | — |
| 3 | 1:2.91:3 | — |
| 4 | 1:1.94:2 | Orange |
| 5 | 1:1.94:2 | White |
| 6 | 1:1.94:2 | Red |
| 7 | 1:1.94:2 | Brown |
| 8 | 1:2.91:3 | Orange |
| 9 | 1:2.91:3 | White |
| 10 | 1:2.91:3 | Red |
| 11 | 1:2.91:3 | Brown |

Suspensions of Case 5 have the highest deviation from the IEP point, as shown in FIG. 1. Case 1, Case 2, and Case 3 suspensions showed an increase in pH value corresponding to increased vol. %. For real life applications, such high alkalinity levels are not favorable due to the potential to corrode pipelines.

Figure 2:
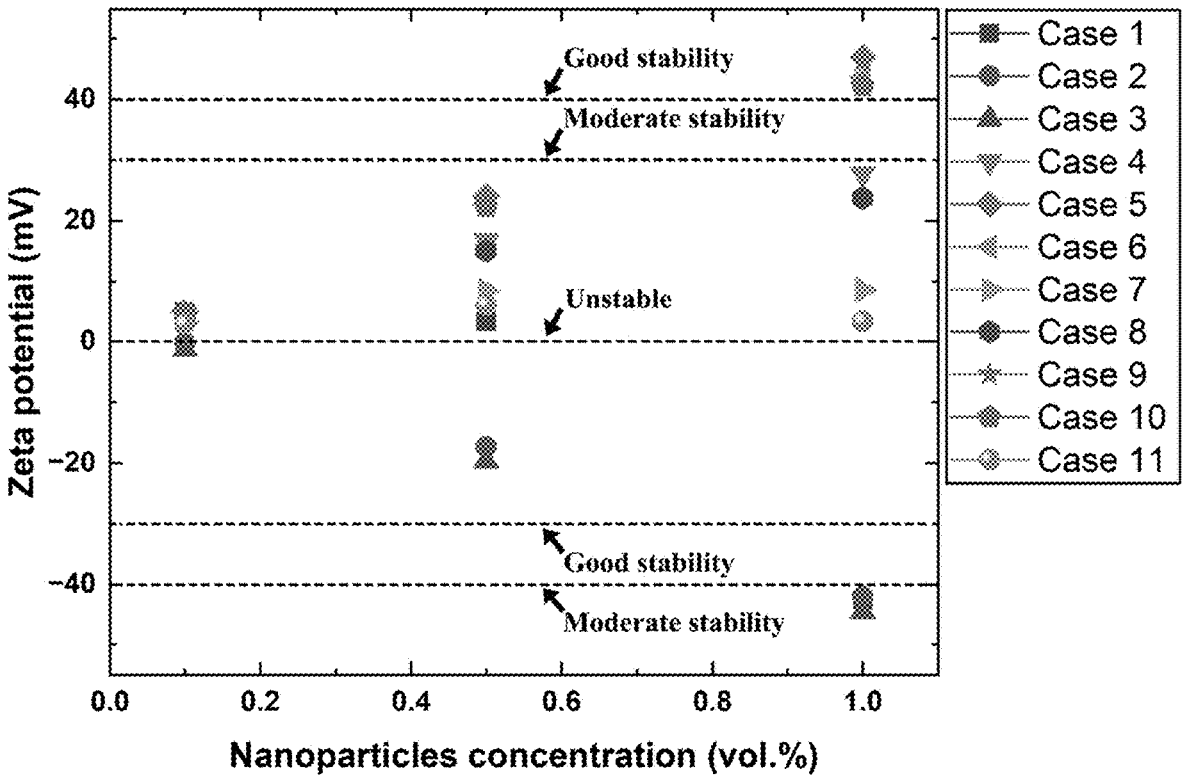
FIG. 2 depicts a graph displaying zeta potential variation and dispersed particle concentration of various examples of the present methods.
Figure 3:
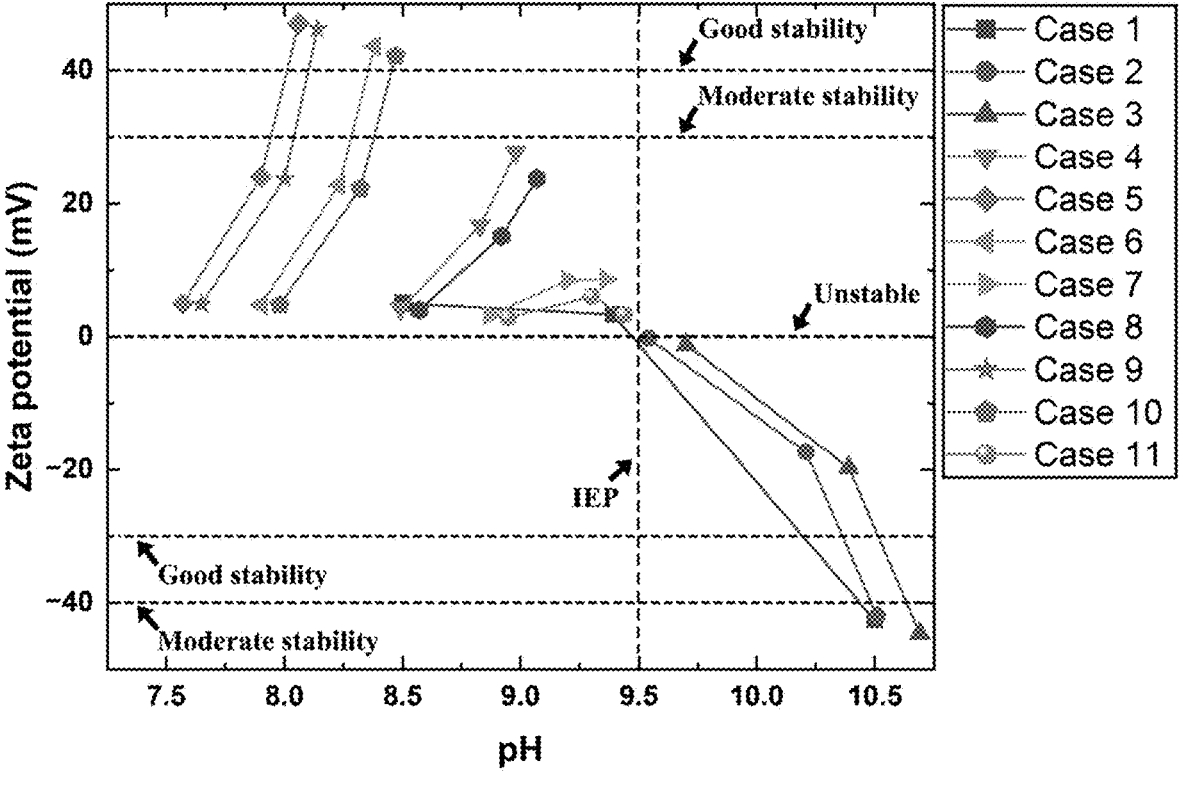
FIG. 3 depicts a graph displaying zeta potential variation and pH variation of various examples of the present methods.

A zeta potential analysis confirmed that Case 5 suspensions outperformed their counterparts in terms of stability improvements, as illustrated in FIG. 2. A zeta potential vs pH plot is shown in FIG. 3 for further comparison, and to confirm the superiority of the Case 5 suspension scenario compared to its counterparts.

In conclusion, all marine-derived biosurfactant infused effervescent tablets showed better dispersion stability and maintained an acceptable pH range for real-life industrial applications, particularly when compared to pure ZnO suspensions. Tablets containing pure effervescent agents only can increase the dispersion stability of the ZnO suspension, but at the cost of increasing the pH levels of the suspensions to unacceptable values.

It is to be understood that the marine organism infused effervescent tablet for producing enhanced suspensions described herein is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. An effervescent tablet comprising:
   a nudibranch mucus biosurfactant;
   zinc oxide (ZnO) powder;
   malic acid; and
   potassium carbonate.

2. The effervescent tablet of claim 1, wherein the nudibranch mucus is obtained from a nudibranch of the species *Dendrodoris fumata*.

3. The effervescent tablet of claim 1, wherein the nudibranch mucus is freeze-dried nudibranch mucus.

4. The effervescent tablet of claim 3, comprising about 0.3 g of freeze-dried nudibranch derived mucus.

5. The effervescent tablet of claim 1, comprising about 5.61 g ZnO powder.

6. The effervescent tablet of claim 1, comprising about 28.05 g ZnO powder.

7. The effervescent tablet of claim 1, comprising about 56.1 g ZnO powder.

8. The effervescent tablet of claim 1, comprising a ratio of 1:1.94:2 zinc oxide powder:malic acid:potassium carbonate by weight.

9. The effervescent tablet of claim 1, comprising a ratio of 1:2.91:3 zinc oxide powder:malic acid:potassium carbonate by weight.

10. A method of making the effervescent tablet of claim 1, the method comprising:
    providing a biosurfactant derived from nudibranch mucus;
    providing a ZnO powder;
    mixing the biosurfactant and the ZnO powder under a first set of controlled conditions to form a first mixture,
    adding malic acid and potassium carbonate to the first mixture to obtain a second mixture;
    mixing the second mixture under a second set of controlled conditions; and
    consolidating the second mixture into tablet form using a hydraulic tablet press to obtain the effervescent tablet.

11. The method of claim 10, wherein the nudibranch mucus comprises powdered, freeze-dried nudibranch mucus.

12. The method of claim 10, comprising mixing about 0.3 g of freeze-dried nudibranch derived biosurfactant with about 5.61 g, about 28.05 g, or about 56.1 g ZnO powder to obtain the first mixture.

13. The method of claim 10, comprising mixing the biosurfactant and the ZnO powder using a mortar and pestle for about 10 minutes to about 20 minutes at a temperature of about 20° C. to about 27° C. and at a humidity of about 30% to about 50%.

14. The method of claim 10, comprising mixing the second mixture using a mortar and pestle for about 5 minutes to about 10 minutes under an inert gas at a temperature between about 20° C. and about 27° C., and at about zero % humidity.

15. The method of claim 10, comprising consolidating the second mixture into tablet form using a hydraulic tablet press under 100 kN to obtain the effervescent tablet.

16. The method of claim 10, comprising adding the effervescent tablet to 1 L of deionized water (DIW) to start a chemical reaction resulting in the formation of a 0.1 vol. %, 0.5 vol. %, or 1 vol. % suspension.

17. A method of making a suspension, the method comprising:

providing a ZnO powder;

adding malic acid and potassium carbonate to the ZnO powder to obtain a mixture;

mixing the mixture under a set of controlled conditions;

consolidating the mixture into tablet form using a hydraulic tablet press to obtain the effervescent tablet;

adding about 1 wt % concentrated nudibranch mucus to 1 liter of deionized water;

sonicating the deionized water including the concentrated nudibranch mucus for about 1 hour to obtain a sonicated mixture; and adding the effervescent tablet to the sonicated mixture of deionized water and concentrated nudibranch mucus to obtain a suspension.

18. The method of claim 17, comprising mixing the mixture using a mortar and pestle for about 5 minutes to about 10 minutes under an inert gas at a temperature between about 20° C. and about 27° C., and at about zero % humidity.

19. The method of claim 17, comprising consolidating the mixture into tablet form using a hydraulic tablet press under 100 kN to obtain the effervescent tablet.

\*   \*   \*   \*   \*